(12) United States Patent
Lashina et al.

(10) Patent No.: US 10,071,220 B2
(45) Date of Patent: Sep. 11, 2018

(54) SELECTION OF AMBIENT STIMULI

(71) Applicant: KONINKLIJKE PHILIPS N.V., Eindhoven (NL)

(72) Inventors: Tatiana Aleksandrovna Lashina, Eindhoven (NL); Jan Johannes Gerardus De Vries, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 403 days.

(21) Appl. No.: 14/383,908

(22) PCT Filed: Mar. 27, 2013

(86) PCT No.: PCT/IB2013/052422
§ 371 (c)(1),
(2) Date: Sep. 9, 2014

(87) PCT Pub. No.: WO2013/144854
PCT Pub. Date: Oct. 3, 2013

(65) Prior Publication Data
US 2015/0031942 A1    Jan. 29, 2015

Related U.S. Application Data

(60) Provisional application No. 61/616,028, filed on Mar. 27, 2012.

(51) Int. Cl.
*A61M 21/02*    (2006.01)
*A61B 5/16*    (2006.01)
(Continued)

(52) U.S. Cl.
CPC .............. *A61M 21/02* (2013.01); *A61B 5/024* (2013.01); *A61B 5/0402* (2013.01);
(Continued)

(58) Field of Classification Search
CPC ........ A61M 2230/005; A61M 2230/06; A61M 2230/42; A61M 2230/04; A61B 5/16; A61B 5/486
See application file for complete search history.

(56) References Cited

U.S. PATENT DOCUMENTS 5,465,729 A    11/1995    Bittman et al.
5,676,633 A    10/1997    August
(Continued)

FOREIGN PATENT DOCUMENTS

CN    1723839 A    1/2006
JP    H10118185 A    5/1998
(Continued)

OTHER PUBLICATIONS

Ulrich, R.S. et al. "A review of the research literature on evidence based healthcare design." White Paper Series 5 of 5. Publisher: The Center for Health Design and Georgia Institute of Technology. Publication date: Sep. 1, 2008.
(Continued)

*Primary Examiner* — Christine H Matthews

(57) ABSTRACT

In summary the invention relates to a stimuli control system configured for finding ambient stimuli from a database in a way so that the ambient stimuli having the most promising effect on stress reduction is selected. The selection may be performed based on a probability distribution created for describing how likely it is that a given ambient stimuli has a positive effect on the stress level for a given patient or other user. The database is a multiuser database which may be updated based on experiences from users' already registered ambient stimuli.

10 Claims, 2 Drawing Sheets

(51) Int. Cl.

| | |
|---|---|
| *A61B 5/024* | (2006.01) |
| *A61B 5/0402* | (2006.01) |
| *A61B 5/0476* | (2006.01) |
| *A61B 5/0488* | (2006.01) |
| *A61B 5/053* | (2006.01) |
| *A61M 21/00* | (2006.01) |
| *G06F 19/00* | (2018.01) |
| *G16H 50/70* | (2018.01) |

(52) U.S. Cl.
CPC .......... *A61B 5/0476* (2013.01); *A61B 5/0488* (2013.01); *A61B 5/0533* (2013.01); *A61B 5/165* (2013.01); *A61M 2021/005* (2013.01); *G06F 19/321* (2013.01); *G06F 19/3418* (2013.01); *G16H 50/70* (2018.01)

(56) References Cited

U.S. PATENT DOCUMENTS

| | | | |
|---|---|---|---|
| 6,102,846 | A | 8/2000 | Patton et al. |
| 6,520,905 | B1 * | 2/2003 | Surve ............... A61B 5/16 434/236 |
| 6,607,484 | B2 | 8/2003 | Suzuji et al. |
| 6,798,898 | B1 | 9/2004 | Fedorovskaya et al. |
| 6,870,673 | B2 | 3/2005 | Cromer et al. |
| 8,617,044 | B2 | 12/2013 | Pelgrim et al. |
| 8,672,852 | B2 | 3/2014 | Gavish |
| 2001/0049471 | A1 | 12/2001 | Suzuki et al. |
| 2004/0024287 | A1 * | 2/2004 | Patton et al. ......... A61M 21/00 600/27 |
| 2007/0167690 | A1 | 7/2007 | Miyazaki et al. |
| 2011/0109879 | A1 | 5/2011 | Palti-Wasserman et al. |
| 2012/0016208 | A1 | 1/2012 | Janssen et al. |
| 2012/0077162 | A1 | 3/2012 | Veen et al. |

FOREIGN PATENT DOCUMENTS

| | | |
|---|---|---|
| JP | 2005305132 A | 11/2005 |
| JP | 2010264038 A | 11/2010 |

OTHER PUBLICATIONS

Zwaang, M.D. "Directing affect through music". Technical Note TN-2007100608. Philips Research Eindhoven (2008), Eindhoven, Netherlands.

Topf, M. "Hospital noise pollution: an environmental stress model to guide research and clinical interventions", Journal of Advanced Nursing vol. 31, Issue 3, pp. 520-528, Mar. 2000.

Dijkstra, K. et al. "Individual differences in reactions towards color in simulated healthcare environments: The role of stimulus screening ability". Journal of Environmental Psychology vol. 28, Issue 3, Sep. 2008, pp. 268-277.

Joye, Y. "A tentative argument for the inclusion of nature-based forms in architecture". Proefschrift neergelegd tot het behalen van de graad van Doctor in de Wijsbegeerte Universiteit Gent Faculteit Letteren en Wijsbegeerte Maart, 2007.

Dijkstra, K. et al. "Physical environmental stimuli that turn healthcare facilities into healing environments through psychologically mediated effects: systematic review". Journal of Advanced Nursing. 2006:56(2): 166-181.

Parsons, R. et al. "The view from the road: Implications for stress recovery and immunization." Journal of Environmental Psychology, (1998) 18, 113-139.

Dijk, E. et al. "Audio-tactile stimuli to improve health and well-being—a preliminary position paper," Special Symposium at EuroHaptics 2010, Haptic and Audio-Visual Stimuli: Enhancing Experiences and Interaction, pp. 1-10, Amsterdam, Jul. 7, 2010.

Knez, I. et al. "Effects of indoor lighting, gender, and age on mood and cognitive performance." Environment and Behavior, 6, 817-831. 2000).

Van Den Berg, A. "Health impacts of healing environments: A review of the benefits of nature, daylight, fresh air and quiet in healthcare settings." Groningen: Foundation 200 years University Hospital Groningen (2005).

Villmann, T. et al. "Divergence Based Online Learning in Vector Quantization." Artificial Intelligence and Soft Computing, Lecture Notes in Computer Science, 2010, vol. 6113/2010, 479-486.

* cited by examiner

SELECTION OF AMBIENT STIMULI

CROSS-REFERENCE TO PRIOR APPLICATIONS

This application is the U.S. National Phase application under 35 U.S.C. § 371 of International Application No. PCT/IB2013/052422, filed on Mar. 27, 2013, which claims the benefit of U.S. Provisional Application No. 61/616,028, filed on Mar. 27, 2012. These applications are hereby incorporated by reference herein.

FIELD OF THE INVENTION

The invention relates to a control system for selecting ambient stimuli from a database, in particular to such a control system for use in a hospital environment.

BACKGROUND OF THE INVENTION

Ambient stimuli such as special light settings, presentation of music and video may be used in hospitals to reduce patient's stress. However, the potential stress reduction offered by such ambient stimuli is dependent on individual differences between patients. Thus, it is a problem for ambient stimuli systems that they do not enable adaptation of the presented ambient stimuli to a patient.

Accordingly, it is not straightforward to select an ambient stimulus for a patient. Thus, it would be desirable to be able to better choose the most effective ambient stimuli in terms of stress reduction for a given patient.

U.S. Pat. No. 6,102,846 discloses method of managing a psychological and physiological state of an individual which involves the use of images or stimuli, the measurement of a physiological state of the individual, and the creation of a personalized preferred response profile which is specifically tailored to the individual. With the method it is possible for an individual to manage and thereby lower his or her stress by viewing, for example, images which are selected based on the created personalized preferred response profile for the individual. The personalized preferred response profile is created by having the individual view, for example, a wide variety of images and creating the profile based on those images which provide a preferred response to the individual. The system supports and enhances existing biofeedback equipment.

The inventor of the present invention has appreciated that an improved method for selection of ambient stimuli is of benefit, and has in consequence devised the present invention.

SUMMARY OF THE INVENTION

It would be advantageous to achieve improvements within use of ambient stimuli for stress reduction. In general, the invention preferably seeks to mitigate or alleviate the disadvantages relating to current methods used for generating ambient stimuli for patients where little or no adaptation of the stimuli to the patient is used. In particular, it may be seen as an object of the present invention to provide a method that solves the above mentioned problems of current ambient stimuli systems, or other problems, of the prior art.

To better address one or more of these concerns, in a first aspect of the invention a stimuli control system for selecting ambient stimuli for a user from a database with selectable ambient stimulus descriptors obtained from multiple other users characterized by user characteristics wherein an ambient stimulus descriptor defines an ambient stimulus and has an associated user characteristic and an associated stress reduction capability is presented, comprising:
  an input for receiving an input user characteristic,
  a filter function configured for determining a selection of ambient stimulus descriptors from the database by filtering the ambient stimulus descriptors with respect to the input user characteristic,
  a selecting function configured for selecting at least one ambient stimulus descriptor from the determined selection of ambient stimulus descriptors in dependence of the stress reduction capabilities.

A stimulus descriptor may be a data record which defines a particular ambient stimulus, e.g. a music stimulus. The stimulus descriptor has an associated user characteristic, e.g. age and gender, and an associated stress reduction capability, i.e. a capability of the ambient stimulus to reduce stress. Thus, a stimulus descriptor may be seen as a data record or other data structure defining an ambient stimulus and containing a user characteristic and a stress reduction capability.

By filtering the database with respect to the user characteristics a selection from the database is generated which contains stimulus descriptors having associated user characteristics which are close to the input user characteristics. The filtering may comprise determining stimulus descriptors having user characteristics which are similar to the input user characteristics.

The selecting function is configured for selecting at least one stimulus descriptor, i.e. by selecting a stimulus descriptor an ambient stimulus is selected for the user. Accordingly, by selecting an ambient stimulus from the selection having promising stress reduction capabilities for user's with user characteristics corresponding to the current user's characteristics an improved ambient stimulus selection may be achieve and, therefore, improved stress reduction.

In an embodiment the selecting function is configured for selecting the at least one ambient stimulus descriptor in random from the determined subset and in dependence of the stress reduction capabilities. Thereby, the user is advantageously presented with different ambient stimuli over time.

In an embodiment the stimuli control system further comprises:
  an input for receiving a physiological measurement, and
  a translator for translating the physiological measurement into a stress level, wherein
  the filter function is configured for determining the selection of ambient stimulus descriptors from the database by additionally filtering the ambient stimulus descriptors with respect to the stress level.

By additionally basing the filtered selection of the stimulus descriptors on a current stress level of the user improved selection of ambient stimuli to the user may be achieved since the different ambient stimuli may be suited for high and low stress levels.

Alternatively, the filter function may be configured for determining a second selection or subset of ambient stimulus descriptors from the database by filtering the stimulus descriptors with respect to the stress level. In this case selecting at least one stimulus descriptor from the determined first and second selections/subsets in dependence of the stress reduction capabilities of at least some of the stimulus descriptors of the first and second selections/subsets may comprise making a combination (e.g. weighted sum) of the stress reduction capabilities of corresponding (i.e. similar but not necessarily identical) stimulus descriptors of the first and second subsets.

In an embodiment the stimuli control system further comprises:
an input for receiving user preferences, wherein
the filter function is configured for determining the selection of ambient stimulus descriptors from the database by additionally filtering the ambient stimulus descriptors with respect to the user preferences.

By additionally basing the filtered selection of the stimulus descriptors on user preferences an improved adaptation of ambient stimuli to the user may be achieved since the different ambient stimuli may be suited for users with different preferences, e.g. preferences for a particular music genre.

In an embodiment the stimuli control system further comprises:
an evaluation function for determining the effect on stress level of a user in response to an executed ambient stimuli, and
a feedback function for supplying data containing information about the executed ambient stimuli, the effect on stress level and the input user characteristic to the database.

By supplying data back to the database which contains information about the stress reduction capabilities together with associated input user characteristic (and/or the stress level determined from the translator and/or user preferences and/or predicted stress level (based on data from similar users)) the database may continuously be updated so that the capability of selecting the ambient stimuli to users is continuously improved.

In an embodiment the stimuli control system is configured for normalizing the effect on the stress level according to the user. Thereby, the stress reduction capabilities of different ambient descriptors may become more or less independent on user characteristics such as weight.

In a related embodiment the stimuli control system is further configured for normalizing the physiological measurements for an individual user so as to enable comparison of the physiological measurements with other users' physiological measurements.

In an embodiment the stimuli control system is configured for representing each of the ambient stimulus descriptors in terms of quantified features of one or more ambient stimuli. Furthermore, the stimuli control system is configured for representing—the quantified features of the ambient stimulus descriptors in a feature space having dimensions corresponding to the features of the ambient stimulus descriptors. The representation of ambient stimuli in a feature space may improve e.g. comparison of different ambient stimuli. In an embodiment the stimuli control system is configured for providing all ambient stimulus descriptors of the selection which have positive stress reduction capabilities with a function, e.g. a Gaussian function, that extrapolates the positive stress reduction capabilities to similar ambient stimulus descriptors, and for determining a probability distribution describing the possibility of positive stress reduction by combining the functions, e.g. by taking their normalized sum, and
the selecting function is configured for selecting the at least one stimulus descriptor from the determined selection in dependence of the probability distribution.

In an embodiment the stimuli control system is configured for averaging the stress level over time. Thereby, temporary effects on the stress level, e.g. caused by a short visit of a doctor, does not affect the selection of ambient stimuli significantly.

In an embodiment the selecting function is configured for randomized selection of the at least one stimulus descriptor from the determined subset over time.

A second aspect of the invention relates to an ambient stimuli system comprising:
a database with selectable ambient stimulus descriptors obtained from multiple users characterized by user characteristics, wherein an ambient stimulus descriptor defines an ambient stimulus and has an associated user characteristic and an associated stress reduction capability, and
a stimuli control system according to the first aspect.

A third aspect of the invention relates to a method for selecting ambient stimuli for a user from a database with selectable ambient stimulus descriptors obtained from multiple other users characterized by user characteristics, wherein an ambient stimulus descriptor defines an ambient stimulus and has an associated user characteristic and an associated stress reduction capability comprising the steps of:
receiving an input user characteristic,
filtering the ambient stimulus descriptors with respect to the input user characteristic for determining a selection of ambient stimulus descriptors from the database,
selecting at least one stimulus descriptor from the determined selection of ambient stimulus descriptors in dependence of the stress reduction capabilities.

In summary the invention relates to a method for finding ambient stimuli from a database in a way so that the ambient stimuli having the most promising effect on stress reduction is selected. The selection may be performed based on a probability distribution created for describing how likely it is that a given ambient stimuli has a positive effect on the stress level for a given patient or other user. The database is a multiuser database which may be updated based on experiences from users with already registered ambient stimuli.

In general the various aspects of the invention may be combined and coupled in any way possible within the scope of the invention. These and other aspects, features and/or advantages of the invention will be apparent from and elucidated with reference to the embodiments described hereinafter.

BRIEF DESCRIPTION OF THE DRAWINGS

Embodiments of the invention will be described, by way of example only, with reference to the drawings, in which.

DESCRIPTION OF EMBODIMENTS

Figure 1:
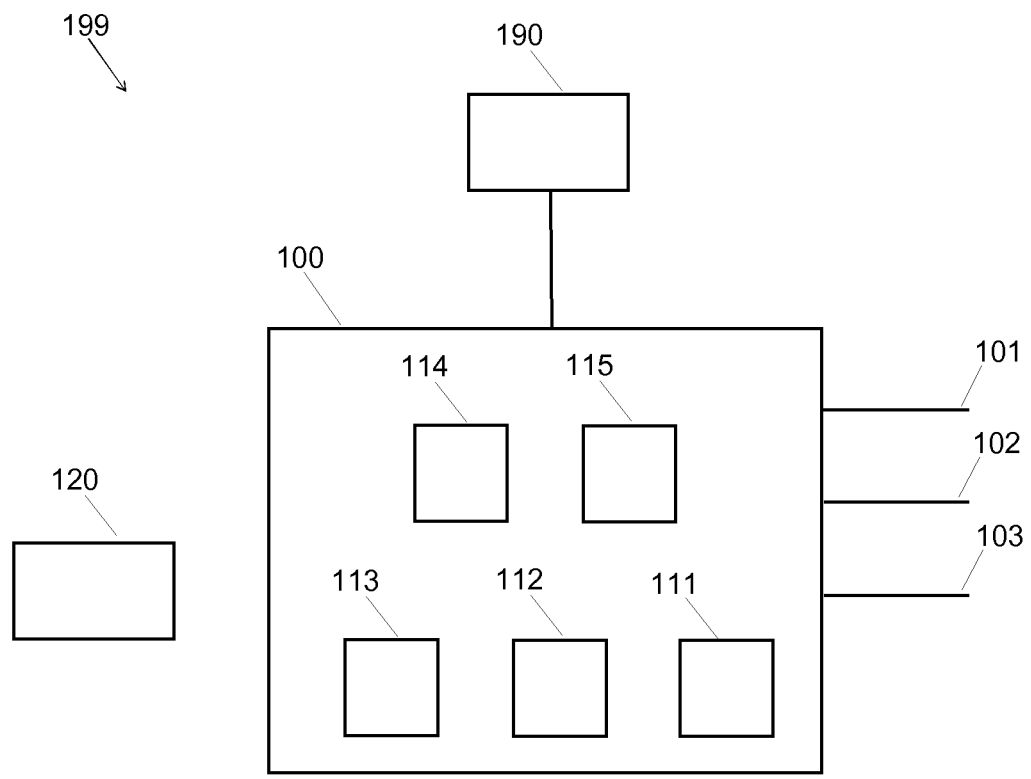
FIG. 1 illustrates an ambient stimuli system 199 comprising a stimuli control system 100 and a database 120 with selectable ambient stimulus descriptors.

FIG. 1 shows a stimuli control system 100 for selecting ambient stimuli for a user, e.g. a patient in a caregiving environment such as a hospital.

The ambient stimuli may be a special room lighting characterized for example by specific light colors and/or a specific light intensity. The ambient stimuli could also be images or video presentations on a display, sound presentations such as nature sounds or music or other stimuli which may have an effect on the user's stress level, e.g. anxiousness, caused by the environment of a hospital and/or actions performed in a hospital or expectations thereof. Additional benefit of stress reduction is that it has been demonstrated that stress reduction has a positive effect by reducing pain in patients, reducing need in medications and promoting patient recovery.

The ambient stimuli are effectuated by stimuli generating devices 190 such as a general lighting installation in a room, an ambient lighting system configured specifically for generating a special light atmosphere, an audio system, a video system, a display or other systems capable of creating ambient changes.

One or more ambient stimuli, e.g. a light color setting and a video presentation, are selected from a database 120 which contains selectable ambient stimulus descriptors. For example, a descriptor for a specific ambient light setting may have a distinguishable name and define properties of the light setting.

The ambient stimulus descriptors in the database 120 have been obtained from situations where other users have been exposed to ambient stimuli. In connection with the exposure to ambient stimuli the effect on the stress of the user is determined. The effect on the user's stress is recorded in the database 120 as a stress reduction capability for that ambient stimuli exposure together with a user characteristic of the user. The user characteristic may include different characteristics such as age, gender, race, current disease, current use of medication, etc.

Accordingly, the database 120 contains different stimulus descriptors, where each descriptor is associated with a user characteristic, e.g. a patient characteristic, and a stress reduction capability for the user characteristic of a user or users with the same characteristic. Clearly, a descriptor also defines an ambient stimulus.

The stimuli control system 100 further comprises an input 101 for receiving input user characteristics, i.e. characteristics corresponding in format to the user characteristics in the database 120.

An embodiment of the invention also relates to an ambient stimuli system 199 comprising a database 120 with selectable ambient stimulus descriptors and the stimuli control system 100.

Based on the received user characteristics, e.g. for a new patient in a hospital, the control system 100 is capable of finding an ambient stimuli from the database which has shown good stress reduction capabilities for other users having patient characteristics similar to the patient characteristic of the new patient.

In order to achieve this, the system 100 has a filter function 113 which is capable of initially determining a subset of ambient stimulus descriptors from the database 120 by filtering the stimulus descriptors with respect to the input user characteristics so as to find stimulus descriptors having associated user characteristics which are close to the input user characteristics.

Additionally, as an example, a stress reduction probability function that determines the predicted stress reduction effect on the user in question based on the a priori physiological measurements of most similar users may be used in the filter function for determining the subset.

The filtering may be achieved by searching in the database for user characteristics which are close to the input user characteristics. For example, a database stimulus descriptor having an associated user age of 50 may be considered close to an input age of 48.

The ambient stimuli for the new patient is finally determined by a selecting function 112 configured for selecting at least one stimulus descriptor from the determined subset in dependence of the stress reduction capabilities of the descriptors. Thus, since the stimulus descriptors are linked with stress reduction capabilities obtained from other users, one or more stimulus descriptors can be selected for the new patient, by selecting one or more of the descriptors having the highest values of stress reduction capabilities, having values of stress reduction capabilities above a given threshold, or using the stress reduction capabilities as measure of probability for selection. For example, one stimulus descriptor defining an ambient light setting and/or one stimulus descriptor defining a scene of a video presentation could be selected.

In order to avoid that a user is exposed to the same ambient stimuli over time the selecting function 112 may be configured to select stimulus descriptors in random from the determined subset and in dependence of the stress reduction capabilities. A threshold value of the stress reduction capabilities may be set to ensure that the randomly selected stimulus descriptors have a sufficiently high value of stress reduction capabilities. Alternatively, in order to avoid that a user is exposed to the same ambient stimuli over time the selecting function 112 may be configured to exclude stimulus which have been selected to the same user within a given preceding period of time.

In order to further improve adaptation of the selected ambient stimuli it may be advantageous to also select ambient stimulus descriptors in dependence of the current stress level of a patient.

For that purpose the stimuli control system 100 may be provided with an input 102 for receiving physiological measurements of the user and a translator 111 for translating the physiological measurements into stress levels. Suitable physiological measurements may be measurements of heart rate using a pulse detector, skin conductance corresponding to a sweat level using a galvanic skin response sensor, electrical muscle potential using an electromyograph, electrocardiogram using an electrocardiograph, encephalogram using a encephalograph and other measurements. The physiological measurements are converted into stress levels using the stress level translator 111.

As an example the translator 111 may apply a transformation function to measured physiological signals to translate them into a stress indication. As an example, skin conductance is known to correlate positively with stress. The translator 111 can directly translate skin conductance into a relative stress measure by taking the first derivative of the skin conductance signal. In order to provide absolute stress levels, the translator 111 might use historical measurements to compare the current measure, using e.g., baseline comparison, normalization using a histogram or range of previous values, or another method for normalization. For example, the current skin conductance level can be compared to the skin conductance values measured in the past hour, or another time period, and the position of the current skin conductance level within the historic range indicates an absolute stress level. Other physiological signals may require other translation methods for converting them into stress levels, including other normalization methods.

For the purpose of selecting an additional subset of ambient stimulus descriptors from the database 120 in dependence of the determined user stress level the filter function is configured to filter the stimulus descriptor with respect to stress levels.

In order to filter the database descriptors with respect to general user stress levels, at least some of the ambient stimulus descriptors in the database are associated with a user stress level and the user characteristic together with the stress reduction capability for that user characteristic, i.e. for a given user. Clearly, this requires that general stress levels of previous users have been determined and that the general stress levels (i.e. stress levels before exposure to ambient stimuli) are stored in the database 120 together with the effect on the stress (i.e. stress reduction capabilities) in association with a stimulus descriptor (i.e. a descriptor defining the ambient stimuli to which the user has been exposed).

Since the database stimulus descriptors are filtered both with respect to user characteristics and user stress levels the filter function 113 may generate both a first and a second subset of stimulus descriptors. Therefore, the selecting function 112 may be configured for selecting at least one stimulus descriptor from the determined first and second subsets in dependence of the stress reduction capabilities of at least one, normally at least some, of the stimulus descriptors of the first and second subsets.

Alternatively, instead of creating first and second subsets of stimulus descriptors from the database by filtering with respect to the input patient characteristic and the stress level, the filter function 113 may generate a single subset by filtering with respect to the input patient characteristic and the stress level. Thus, in general the filter function 113 is configured to determine a selection of stimulus descriptors from the database, where the selection may be constituted by a single subset or two or more subsets.

The selection by the selecting function 112 of at least one stimulus descriptor from the determined first and second subsets may be performed by making a combination, e.g. a weighted sum, of the stress reduction capabilities of corresponding stimulus descriptors of the first and second subsets. Thus, a common value of a stress reduction capability for a stimulus descriptor of the first subset (which has been obtained by filtering with respect to user characteristics) and for a stimulus descriptor of the second subset (which has been obtained by filtering with respect to a user's general stress level) may be obtained by adding the respective values of stress reduction capabilities. The stimulus descriptors of the first and second subsets need not be the same; for example, the stimulus descriptors could be similar so that both descriptors define ambient light settings which are similar, but not identical, with respect to color and intensity.

In case only a single subset is created by the filter function 113 by filtering with respect to the input patient characteristic and the stress level, the selecting function 112 is configured to select at least one stimulus descriptor from the determined single subset in dependence of the stress reduction capabilities. Thus, in general the selecting function is configured for selecting at least one stimulus descriptor from the determined selection, e.g. a single subset or a plurality of subsets, of stimulus descriptors in dependence of the stress reduction capabilities.

The adaptation of ambient stimuli for a user may be further improved by selecting ambient stimulus descriptors in dependence of user preferences. For that purpose the stimuli control system 100 may be provided with an input 103 for receiving user preferences, e.g. preferences for styles of music, artists and video genres.

Handling of inputted user preferences is provided by the filter function 113 which is further configured for determining a third subset of ambient stimulus descriptors from the database 120 by filtering the stimulus descriptors with respect to the user preferences, and the selecting function 112 which is configured for selecting at least one stimulus descriptor from the determined first, second and third subsets in dependence of the stress reduction capabilities of at least one or some of the stimulus descriptors of the first, second and third subsets. Alternatively, as explained above a single subset of ambient stimulus descriptors may be determined by the filter function 113 by filtering with respect to the user characteristics, the stress level and the user preferences; and the selecting function 112 may determine at least one stimuli descriptor from the subset in dependence of the stress reduction capabilities.

Similarly to the embodiment where stimulus descriptors are filtered with respect to measured stress levels of a user, in the embodiment where stimulus descriptors are filtered with respect to user preferences a stimulus descriptor may be selected from the determined first, second and third subsets, the single subset or generally from a selection in dependence of the stress reduction capabilities of at least some of the stimulus descriptors of the first second and third subsets or the selection by combining (e.g. averaging or summing) values of stress reduction capabilities of stimulus descriptors of the first, second and third subsets or the selection of stimulus descriptors.

Although FIG. 1 shows three inputs 101-103 for receiving user characteristics, values of physiological measurements and data of user preferences, these inputs could also be supplied to the stimuli control system 100 via any other number of inputs such as a single input.

In order to provide a learning function where the database 120 is provided with different ambient stimuli and associated values of stress reduction capabilities for different patient parameters including any combination of patient characteristics, indirectly measured stress levels and user preferences, the stimuli control system is provided with an evaluation function 114 for determining the effect on stress level of a user in response to an executed ambient stimuli and a feedback function 115 for supplying data containing information about the executed ambient stimuli, the effect on stress level (stress reduction capability) and one or more of the 1) input user characteristic, 2) determined the stress level (before or during exposure to ambient stimuli and, 3) user preferences to the database 120.

For the learning function which is embodied by the evaluation function 114 and the feedback function 115 the ambient stimuli to be stored in the database 120 may have been determined by the stimuli control system 100 or determined otherwise, e.g. manually. The effect on stress level and/or the general stress level (e.g. before exposure to ambient stimuli) may have been determined via physiological measurements and the stress translator 111, or the effect on stress or general stress could have been determined manually via user input.

The effect on the stress level which is determined by the evaluation function 114 may be normalized according to the user. The normalization may be required in order to make the stress reduction capabilities of different stimulus descriptors comparable. For example, stress reduction capabilities may be normalized by using historical measurements for comparison with the current measure, using e.g., baseline comparison, normalization using a histogram or range of previous values, or another method for normalization. For example, a level of stress reduction capabilities can be compared with levels of stress reduction capabilities measured in the past hour, or another time period, and the position of the stress reduction level relative to the historic range indicates an absolute stress level. The normalization of the effect on the stress level may be performed by the evaluation function 114, or generally by the stimuli control system 100, e.g. by a processor 116, such as a data or computer processor comprised by the stimuli control system.

In a possible embodiment the ambient stimulus descriptors are represented in terms of quantified features of one or more ambient stimuli. For example, an ambient stimulus descriptor for a piece of music may be represented by the frequency distribution of the audio used, and an ambient light setting may be represented by the light intensities, color or color temperature used for a set of light sources. Other representations include frequency distribution of dynamics (rapid versus slow changes in sounds/images/light-effects, categories of audio/video, textual descriptors, e.g. textual descriptors of nature scenes, genre for music, or other features that helps in discriminating dissimilar atmospheres.

The quantified features of the ambient stimulus descriptors may be represented in a feature/vector space having dimensions corresponding to the features of the ambient stimulus descriptors. Thus, the quantified features of the ambient stimulus descriptors may be combined into a vector describing the atmosphere. The representation or conversion of ambient stimuli into quantified features representation in a feature space may be performed by the stimuli control system 100, e.g. by the processor 116 comprised by the stimuli control system.

In a practical implementation each of the ambient stimulus descriptors of a selection of ambient stimulus descriptors, e.g. of any of the determined first, second and third subsets of stimulus descriptors, are provided with a probability function describing the probability that the ambient stimuli will have a positive effect on stress of the user. For example such a probability function could be created by providing each stimulus descriptor having a positive stress reduction effect (stimulus descriptors from a selection of stimulus descriptors) with a function (referred to as kernel function; e.g., a Gaussian function or other probability function) that extrapolates the positive effect to similar stimulus descriptors (i.e., stimuli descriptors with similar feature values). A probability distribution is then taken by combining the probability functions (e.g. kernel functions), e.g., by taking their normalized sum. By doing so, the known effects of used stimuli can be used to infer expected effects of unused stimuli represented in the vector space. The similarity between stimulus descriptors can be determined from distances between stimulus descriptors in the feature space/vector space, e.g. by determining the Euclidean distance between stimulus descriptors. The assignment of functions to the ambient stimulus descriptors of the selection which have positive stress reduction capabilities, and the determination of a probability distribution from the functions may be performed by the stimuli control system 100, e.g. by the processor 116 comprised by the stimuli control system.

The selecting function 112 may be configured for selecting the at least one stimulus descriptor from the determined selection in dependence of the probability distribution determined according to the above example. For example, the selecting function 112 may be configured for selecting at least one stimulus descriptor from the determined first, second and third subsets in dependence of a weighted sum of the probability distributions over the first, second and third subsets.

In an embodiment the stress level determined by the translator 111 is averaged over time in order to avoid that that sudden and temporary disturbances, e.g. talking to a doctor, to the user influences the selection of ambient stimulus descriptors. The averaging may be performed by the translator or the processor 116 comprised by the stimuli control system.

In another embodiment the selecting function 112 is configured for randomizing selecting of the at least one stimulus descriptor from the determined first, second and/or third subset over time in order to avoid that patient are always provided with the same ambient stimuli.

In any of the above mentioned examples it should be understood that even though an example describes determination of a selection in the form of one or more subsets, e.g. first, second and third subsets, by use of the filter function 113, such an example applies equivalently to determination of a single subset, i.e. a selection, of ambient stimulus descriptors determined by filtering with respect to e.g. user characteristics and a stress level. The selection function 112 is adapted correspondingly for selection of an ambient stimulus descriptor from the selection.

Figure 2:
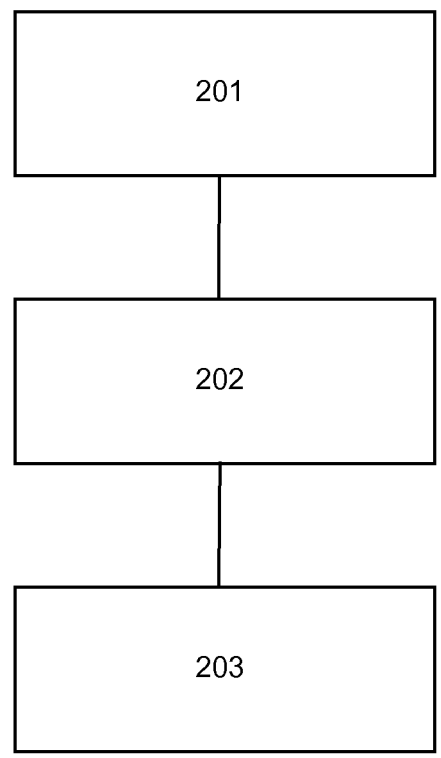
FIG. 2 illustrates a method of the invention with steps 201-203 for selecting ambient stimuli.

FIG. 2 illustrates a method of the invention for selecting ambient stimuli comprising the steps,
- 201 for receiving an input user characteristic,
- 202 for filtering the stimulus descriptors with respect to the input patient characteristic for determining a selection of ambient stimulus descriptors from the database,
- 203 for selecting at least one stimulus descriptor from the determined selection of ambient stimulus descriptors in dependence of the stress reduction capabilities.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

The invention claimed is:

1. A stimuli control system for selecting ambient stimuli for a user from a database with selectable ambient stimulus descriptors, comprising:
   an input for receiving an input user characteristic,
   a filter function configured for determining a selection of ambient stimulus descriptors from the database,
      wherein each ambient stimulus descriptor is a data structure comprising an ambient stimulus, at least one user characteristic, and a value of a stress reduction capability of the ambient stimulus with respect to the at least one user characteristic,
      wherein the ambient stimulus descriptors comprise user characteristics from multiple other users having values of a stress reduction capability corresponding to at least one of the user characteristics of the multiple other users,
      wherein the filter function determines the selection of ambient stimulus descriptors which correspond to the input user characteristic by filtering the ambient stimulus descriptors with respect to the input user characteristic and the user characteristics of the multiple other users,
   a selecting function configured for selecting at least one ambient stimulus descriptor from the determined selection of ambient stimulus descriptors in dependence of the stress reduction capability, an evaluation function configured for determining an effect on stress level of a user in response to an executed ambient stimuli, and a feedback function configured for supplying data containing information about the executed ambient stimuli, the effect on stress level and the input user characteristic to the database, wherein the stimuli control system is configured for normalizing the effect on the stress level according to the user.

2. The stimuli control system of claim 1, where the selecting function is configured for selecting the at least one ambient stimulus descriptor in random from the determined selection and in dependence of the stress reduction capability.

3. The stimuli control system of claim 1, further comprising:

an input for receiving a physiological measurement, and a translator for translating the physiological measurement into a stress level, wherein the filter function is configured for determining the selection of ambient stimulus descriptors from the database by additionally filtering the ambient stimulus descriptors with respect to the stress level.

4. The stimuli control system of claim 3, further comprising: an input for receiving user preferences, wherein the filter function is configured for determining the selection of ambient stimulus descriptors from the database by additionally filtering the ambient stimulus descriptors with respect to the user preferences.

5. The stimuli control system of claim 1, wherein the stimuli control system is configured for representing each of the ambient stimulus descriptors in terms of quantified features of one or more ambient stimuli.

6. The stimuli control system of claim 5, wherein the stimuli control system is configured for representing the quantified features of the ambient stimulus descriptors in a feature space having dimensions corresponding to the quantified features of the ambient stimulus descriptors.

7. The stimuli control system of claim 1, wherein the stimuli control system is configured for providing all ambient stimulus descriptors of the selection which have positive stress reduction capabilities with a function that extrapolates the positive stress reduction capabilities to similar ambient stimulus descriptors, and for determining a probability distribution describing a possibility of positive stress reduction by combining the functions, and where the selecting function is configured for selecting the at least one stimulus descriptor from the determined selection in dependence of the probability distribution.

8. The stimuli control system of claim 1, wherein the stimuli control system is configured for averaging the stress level over time.

9. An ambient stimuli system comprising:

a database with the selectable ambient stimulus descriptors including the user characteristics from multiple other users, and a stimuli control system according to claim 1.

10. A method for selecting ambient stimuli for a user from a computer-readable database with selectable ambient stimulus descriptors, comprising the steps of:

receiving, by an input to the database, an input user characteristic, filtering, by the database, the ambient stimulus descriptors for determining a selection of ambient stimulus descriptors from the database, wherein each ambient stimulus descriptor is a data structure comprising an ambient stimulus, at least one user characteristic, and a value of a stress reduction capability of the ambient stimulus with respect to a user characteristic, wherein the ambient stimulus descriptors comprise user characteristics from multiple other users having values of a stress reduction capability corresponding to at least one of the user characteristics of the multiple other users, wherein the selection of ambient stimulus descriptors which correspond to the input user characteristic are determined by filtering the ambient stimulus descriptors with respect to the input user characteristic and the user characteristics of the multiple other users, selecting, by a processor, at least one stimulus descriptor from the determined selection of ambient stimulus descriptors in dependence of the stress reduction capability, determining, by the processor, an effect on stress level of a user in response to an executed ambient stimuli, supplying, by the processor, data containing information about the executed ambient stimuli, the effect on stress level and the input user characteristic to the database, and normalizing, by the processor, the effect on the stress level according to the user.

* * * * *